United States Patent [19]

Zimmermann et al.

[11] 4,269,826

[45] May 26, 1981

[54] PHYSIOLOGICAL PREPARATION CONTAINING LOADED CELLS IN SUSPENSION AND A MAGNETIC AGENT FOR LOCAL CONCENTRATION THEREOF IN A LIVING BODY

[75] Inventors: Ulrich Zimmermann, Jülich; Günter Pilwat, Niederzier, both of Fed. Rep. of Germany

[73] Assignee: Kernforschungsanlage Julich Gesellschaft mit beschrankter Haftung, Jülich, Fed. Rep. of Germany

[21] Appl. No.: 859,563

[22] Filed: Dec. 12, 1977

[30] Foreign Application Priority Data

Dec. 11, 1976 [DE] Fed. Rep. of Germany ....... 2656317

[51] Int. Cl.$^3$ .................... A61K 35/14; A61K 37/48; A61K 43/00
[52] U.S. Cl. .................................. 424/101; 128/1.1; 128/1.3; 424/1; 424/94; 424/106; 435/2
[58] Field of Search .................. 128/1.3; 424/101, 94; 195/1.8

[56] References Cited

U.S. PATENT DOCUMENTS

3,887,698  6/1975  McConnell et al. .................... 424/88

FOREIGN PATENT DOCUMENTS

2326224  5/1974  Fed. Rep. of Germany .
2326161  12/1974  Fed. Rep. of Germany .
2326191  12/1974  Fed. Rep. of Germany .
2405119  9/1975  Fed. Rep. of Germany .

OTHER PUBLICATIONS

R. Kaiser et al., IEEE Transactions on Magnetics, vol. MAG-6, No. 3, Sep. 1970, Some Applications of Ferro-Fluid Magnetic Colloids.
C. Colley et al., Chemical Abstracts 83: 22192e, Liposomes as Carriers in vivo for Methotrexate (1975).
H. Kimelberg, Biochimica et Biophysica Acta, 448, pp. 531–550 (1976), Differential Distribution of Liposome--Entrapped $^3$H-Methotrexate and Labelled Lipids after Intravenous Injection in a Primate.
H. Kimelberg et al., Chemical Abstracts 85: 116483u, The Effect of Entrapment in Liposomes on the In Vivo Distribution of $^3$H-Methotrexate in a Primate (1976).
U. Zimmermann et al., Chemical Abstracts 82: 108324r, Preparation of Erythrocyte Ghosts by Dielectric Breakdown of the Cell Membrane (1975).
U. Zimmermann et al., Chemical Abstracts 81: 75566v, Reversible Di-Electric Breakdown of Cell Membranes in Electrostatic Fields (1974).
U. Zimmermann et al., Chemical Abstracts 85: 29784z, Enzyme Loading of Electrically Homogeneous Human Red Blood Cell Ghosts prepared by *Di-Electric Breakdown* (1976).
T. Nakamura et al., J. of Appl. Physics, vol. 42, No. 4, Mar. 1971, Magneto-Medicine: Biological Aspects of Ferromagnetic Fine Particles, pp. 1320–1324.
R. Newbower, IEEE Transactions on Magnetics, vol. MAG-9, No. 3, Sep. 1973, pp. 447–450, Magnetic Fluids in the Blood.

*Primary Examiner*—Donald G. Daus
*Assistant Examiner*—M. C. Eakin
*Attorney, Agent, or Firm*—Frishauf, Holtz, Goodman and Woodward

[57] ABSTRACT

Magnetic substances in particles of a diameter in the range between 1 and 20 nm are suspended in the physiological solution by which cells are loaded with materials when their cell membranes have increased permeability, the magnetic materials being provided in such dosing, that when the cells are loaded, separated from the loading solution and prepared for use in a fresh physiological solution, thereafter injected to a living body, they can be collected and held fast at a predetermined location, for example, at the location of a tumor, by the effect of an external magnetic field. Ferritin, magnetite, cobalt ferrite, nickel ferrite and other ferrimagnetic, ferromagnetic or even paramagnetic compounds can be incorporated into loaded cells for this purpose.

14 Claims, No Drawings

PHYSIOLOGICAL PREPARATION CONTAINING LOADED CELLS IN SUSPENSION AND A MAGNETIC AGENT FOR LOCAL CONCENTRATION THEREOF IN A LIVING BODY

CROSS REFERENCE TO RELATED APPLICATION

Ser. No. 859,240, filed Dec. 9, 1977.

This invention relates to a process of preparation of a physiological solution containing a mass of loaded cells in suspension, such cells having a concentration of material loaded therein designed for chemical or physical interaction with substances located outside of the cell membrane. In such a process, the permeability of living animal cells of the kind having a cell membrane suspended in a cell-compatible solution is increased by the effect of osmotic pressure or by the effect of an electric field. In such a process, also, the interaction material or materials are drawn out of the surrounding cell-compatible solution by permeation through the cell membranes of which the permeability has been increased with simultaneous exchange with the cell content in the interior of the cells to be loaded, and then the material or materials in question are locked in the cells by regeneration of the cells that heals the changes produced in the cell membrane by the effect of osmotic pressure or by the effect of an electric field, after which the loaded cells are separated from the cell-compatible solution containing the loaded material and are suspended for preservation and storage in a physiological solution having an osmolarity that corresponds to the osmolarity of the content of the loaded cells. The term "osmolarity" refers to a concentration of particles of molecular size in terms of the osmotic pressure, so that the preceding statement refers to a solution in which osmosis will not occur during storage.

Processes of the above kind for preparation of a suspension of loaded cells in a physiological solution are known from German Pat. No. 23 26 224 and from German published patent applications (OS) Nos. 23 26 161 and 24 05 119. The patent just mentioned relates to processes for incorporating of complex-forming materials in loaded cells obtained from living cells of living organisms. The processes disclosed in German (OS) No. 23 26 161 concern the incorporation of catalytically active materials such as enzymes or pharmaceutics in loaded cells. Both of the processes just mentioned seek to increase the permeability of the cell membrane by the action of osmotic pressure on the membrane. In the process disclosed in German (OS) No. 24 05 119, on the other hand, the increase of the permeability is obtained by the effect of an electric field.

In addition to the designation "loaded cells" which is intended to express that the cells are "loaded" with materials that are distinct from the normal cell content, other terms have been used for the products of the known processes of the above-described kind, such as "membrane vesicles", "ghost cells" and "membrane envelopes".

As cells for the known processes for preparing a mass of suspended loaded cells, there are used both cells that occur as individual cells in a physiological solution, as for example erythrocytes, lymphocytes, thrombocytes or leukocytes and also cells, such as for example liver cells that are organized in tissues as associations of cells clinging one to another. The cell binding of a tissue is releasable by biochemical or biophysical procedures, so that in this fashion also a suspension of cells in a solution can be obtained.

In the performance of the known processes, particularly for incorporation of extraneous materials in the loaded cells, a specific property of the membrane of living cells is used, namely that a permeability increase produced within certain limits can be reduced back to normal by healing through regeneration of the cells. The healed membrane of the loaded cells thus regains the semipermeable properties of the membrane of the original cells. Apart from the cases in which materials are used which destroy the membrane after their incorporation in the loaded cells and are thereby set free, it is then possible to bring the material incorporated in the loaded cells into interaction with substances present in a physiological solution outside of the loaded cells without the material incorporated and locked in the loaded cells getting into the physiological solution. This takes place when the loaded cells are immersed into the physiological solution containing the substances in question and the substance, by permeation, fits through the semipermeable membranes of the loaded cells. It is thus possible, for example, with the enzyme invertase locked in loaded cells, to convert cane sugar (sucrose) into glucose and fructose, since cane sugar as well as glucose and fructose get through the membrane, while the enzyme invertase remains locked in the loaded cells. It is also possible, for example, to load cells with urease and then to inject the loaded cells thus produced into the blood vessels of a human body without releasing the urease out of the loaded cells into the blood, and thereby to break down urea contained in the blood which penetrates into the loaded cells.

There is, however, a disadvantage in the masses of loaded cells produced according to the known methods that lies in the fact that the interaction of the special material locked in the loaded cells with substances present in a solution outside the cell membrane extends over the entire volume and extent of the physiological solution, so that the effectiveness of that material cannot be concentrated at a particular or preferred location in the physiological solution where the physiological solution is one that extends through an animal body including portions in various organs of the body. If, for example, loaded cells prepared from erythrocytes are injected in the blood circulation system of a living animal, the loaded cells prepared according to the known methods distribute themselves over the entire blood circulation system, which has the result that the effect of the material locked in the cells is likewise spread out over the entire circulation system. It is quite impossible to provide a limitation of the effect, for example, for a medicament locked into the loaded cells, to a particular location within the circulation system of the body or even in a particular organ of the body when the loaded cells are prepared according to the known methods.

THE PRESENT INVENTION

It is an object of the present invention to provide a process for the preparation of a mass of loaded cells by which a mass can be produced with which it is possible to bring into effect the materials carried along in the loaded cells in a preferred location while they are being circulated in a physiological solution that, for example, may be in the blood flowing in the arteries or veins of an animal body, especially in a particular organ of the animal body.

Briefly, the object of the invention is achieved by providing magnetic substances in particles of a diameter in the range between 1 and 20 nm in the physiological solution by which cells are loaded with materials when their cell membranes have increased permeability, the magnetic materials being provided in such dosing, that when the cells are loaded, separated and prepared for use in a fresh physiological solution, they can be collected and held fast by the effect of an external magnetic field at a predetermined location. The particles of magnetic materials are pre-coated with a silicone film to inhibit damage to the loaded cells.

If, by the process of the present invention, a ferrimagnetic, ferromagnetic or even a paramagnetic compound, (all of which may be referred to as magnetic compounds) as for example cobalt ferrite, nickel ferrite, magnetite or ferritin, is locked into the loaded cells, then it is possible in a simple manner to collect and hold loaded cells inserted into the circulatory system of a living body by a magnetic field applied at a preferred location of the living body and thus to bring the material with which the cells are loaded, which may be pharmaceutical or other materials, such as radionuclides, at this location particularly. For the excitation of a sufficiently strong field gradient of the magnetic field, it can be convenient and effective to provide a magnetized piece of metal coated with a physiologically compatible synthetic material at the particular place at which the loaded cells are to be concentrated.

An advantageous further development of the process of the present invention is presented in the case in which materials which if incorporated along in the loaded cells would lead to a premature destruction of the cell membranes by interaction therewith, which would lead to an uncontrolled liberation of the loading material from the membrane vesicles and thus of a diffusion of the material in the physiological solution, by providing for the incorporation in the loaded cells, together with the principal loading material which is to have a physiological effect, and the magnetic substances above mentioned, further materials which are capable of inhibiting the first-mentioned material that has a tendency to destroy the cell membranes when incorporated in loaded cells. All of these materials can be incorporated in the loaded cells in the usual loading step which takes place when the cells to be loaded have had their permeability increased while immersed in a physiological solution containing the materials to be incorporated into the loaded cells. The materials for inhibiting the effect of some loading materials to interact destructively with the cell membranes are described in our copending patent application Ser. No. 859,240, filed Dec. 9, 1977, and operate by the formation of hydrogen bonds or covalent bonds with the incorporated material which otherwise would have a destructive effect on the cell membranes. Such materials include, as described in the above-mentioned patent application, proteins and sugars (especially polysaccharides). These materials are incorporated in the loaded cells in such dosing that after the several materials are locked into the loaded cells, the interaction of the materials with the cell membrane is inhibited for a predetermined time. In that manner, a premature destruction of the loaded cells is also inhibited where one or more of the materials loaded therein would, if incorporated alone in the loaded cells, lead to premature destruction of the cell membranes, so that such materials can be utilized in the process and resulting product of the present invention where the materials locked in the loaded cells are intended to remain locked into the loaded cells and then collected and held at a preferred location in the physiological solution, either for use as locked into loaded cells there or for subsequent release there when ultimately the membranes of the cells are broken down.

By utilization of the last-mentioned variant of the method of preparation of the process of the present invention, there can be locked into loaded cells, for example, the material 6-fluoro-uracil known as a means for counteracting cancer, and also the magnetic substances discussed above, and finally, the protein albumin or a sugar, for example sucrose, so as to obtain the result that the membranes of the loaded cells last about twice as long as if the albumin or sugar had not been included. Of course, it is possible to obtain the result, by corresponding dosing of the materials delaying the destruction of the cell walls, that the loaded cells remain intact only for a short time.

A particularly useful application of the loaded cell suspension according to the version of the invention just described above is its use in the treatment of tumors. For this purpose, for example, methotrexate, which belongs to the group of compounds that attack folic acid, that today is counted along with alkylating agents as among the most effective substances for the treatment of neoplasia (abnormal swellings, tumors), can be locked into loaded cells along with magnetic material and also with a third material capable of delaying the destruction of the cell membranes as above described. The loaded cells are then injected into the bloodstream of the body and held at the location of the tumor by an externally produced magnetic field. The methotrexate set free after a predetermined time will then develop its effect at the very location of the tumor. In this way, methotrexate is advantageously prevented from being distributed over the entire blood circulation system and developing its effect throughout the living body and thus also attacking healthy tissue. That last mentioned disadvantage could not be prevented in the heretofore ordinary application of methotrexate, in which methotrexate is directly injected into the blood circulation system. With the use of the particular variety of loaded cells provided by the process just mentioned, there is also achieved the advantage that a smaller dose can be introduced into the body than was formerly necessary for the treatment of tumors to produce the same effect, or that a smaller number of injections can be used than were formerly necessary, with the incidental advantage of avoiding undesirable side effects in the use of methotrexate.

Another very advantageous further development of the process of the invention is provided in the case in which the loaded cells are used to set free cell-compatible materials that have no destructive effect on the cell membrane. In this case, along with this material and the magnetic substances there is included in the physiological solution in which the cells are loaded while their membrane permeability is temporarily raised, an agent having a destructive effect on the cell membrane that is present in such dosing that after membrane permeability is brought back to normal by healing and the loaded cells are thereafter from the reagent containing physiological solution, the cell membranes of the loaded cells will be destroyed after a predetermined time. The use of such a material having a destructive effect upon the cell membranes, as for example proteolytic enzymes and substances that break down lipids, typically enzymes such as pronase P, phospholiphase and trypsin, it is possible, for example, after injecting loaded cells into the bloodstream of a living body to collect certain particular materials locked into the loaded cells, as for example tetracycline to which ferritin has been added, by holding the loaded cells at a collected location in the blood circulation system and then to release that material after a predetermined time into the bloodstream. A particularly high effectiveness of the tetracycline thus obtained. It is further possible, of course, to inject a mixture of loaded cells having different doses of the agent destructive of the cell membranes into the bloodstream, in order to control in some predetermined manner the course of the release of the tetracycline or other such material.

Furthermore, in the case of materials that if enclosed alone in the loaded cells would lead to premature destruction of the membranes of the cells, although it would be desirable to release the material from the loaded cells only after a predetermined time, it has been found effective, in accordance with the invention described in my copending application Ser. No. 859,240 to load in the loaded cells also a material which will inhibit the destruction of the cell membranes by the formation of hydrogen bridge bonds or by the formation of covalent bonds with the agent loaded into the cells that tends to destroy the cell membranes, the inhibiting material being introduced in the cell-compatible solution from which the cells are loaded in such a dosing that after healing of the cell membranes and separation of the loaded cells from the solution, the cell membranes of the loaded cells will be destroyed after a predetermined time. It is thus advantageously possible to prevent an uncontrolled release of the material locked into the loaded cells.

A further advantageous development of the process according to the invention consists in that the materials loaded into the cells to provide an interaction with substances outside the cells e.g., tumor-treating agents are introduced into the cell-compatible solution provided for loading of the cells with a coating of liposomes of a diameter in the range of 5 to 20 nm.

Since the liposomes, after their release from the loaded cells immediately get into the tissues on the boundaries of the blood circulation path, it is thus possible to deliver particular materials for action directly in the interior of organs of the body that cannot be reached by capillary blood vessels. All that is necessary for that purpose is to hold the loaded cells in the blood circulation path of the organ in question by the influence of a magnetic field applied externally to the body and then to set free the particular material or the material contained in liposome particles by destruction of the cell membranes.

For the case that the teaching provided in the above-cited German patent and German OS No. 23 26 191 regarding permeability increase by the operation of osmotic pressure, the process of the present invention can be carried out in accordance with the following illustrative procedure:

The cells provided for the preparation of the mass of loaded cells are first put into a cell-compatible solution that, for example, can be a aqueous solution containing at least 0.5 mM per liter of magnesium and/or calcium ions as well as potassium ions, the solution having an osmolarity that is so low compared with the osmolarity of the cell content that, as the result of the osmotic pressure thereby produced in the cells, the permeability of the cell membranes is increased—without however destroying the membranes.

Erythrocytes are used for preparation of the loaded cells. The osmolarity difference to be provided amounts approximately to a factor of 15. If the cell-compatible solution does not already contain the materials to be loaded into the cells, this material should then at this point be added. Furthermore, the materials to be included in the cells in accordance with the present invention are also introduced into the cell-compatible solution in the appropriate dosing. After the material exchange between the materials present in the cell-compatible solution and the cell contents through the cell membranes now having an increased permeability, and the content of the thus produced loaded cells practically corresponds to that of the cell-compatible solution, as a next step, the osmolarity of the cell-compatible solution is increased to that of the original cell content by the addition of osmotically active materials, such as calcium, potassium and sodium ions. By osmotically active materials there are here understood materials that have a reflection coefficient of about 0.8, but, however, because they are in general contained in a cell-compatible solution, build up a sufficiently high osmotic pressure. After a dwell time, during which the cell membranes heal up, the loaded cells so formed are separated from the cell-compatible solution and the mass of loaded cells thus produced is poured into an isotonic physiological liquid. When erythrocytes are used, it is practical, for healing away the changes of the cell membranes produced by permeability increase, to let the cells stand for about five minutes at 0° C. and then to warm them up to body temperature for about 30 to 60 minutes.

For the case in which the teaching of German OS No. 24 05 119 regarding permeability increase by the effect of an electric field is to be used, the performance of the method of the present invention is carried out as follows:

The cells provided for the preparation of the mass of loaded cells are put into an electrically conducting liquid forming a cell-compatible electrolyte solution which is preferably at a temperature lying between 0° C. and 25° C. As a next step, the electrolyte solution containing the cells is subjected to an electric field having a strength from $10^3$ to $10^5$ V/cm until the permeability of the cell membranes is increased to such an extent that molecules with a radius of at least 0.5 nm can pass through the cell membranes. For this purpose, it is convenient and practical to pass the electrolyte solution through a focus of an electric field. The resulting permeability increase can be recognized, for example in the application of the process to erythrocytes, by the discoloration of the electrolyte liquid as the result of the hemoglobin going out of the cell interiors and by the decoloration of the erythrocytes. In the case in which the materials and substances that are to be incorporated in the loaded cells are already in the cell-compatible electrolyte solution, the material exchange takes place right after the permeability increase. It is however also possible, after the permeability increase and still before the performance of the healing of the cell membranes, to put the cells into a cell-compatible solution of which the osmolarity corresponds to the osmolarity of the cell content of the original cells. In this cell-compatible solution, in which are contained the materials to be loaded into the cells, the material exchange between these materials and the cell content then takes place.

After a dwell time in which the cell membranes heal, the loaded cells thus formed are separated from the cell-compatible solution and the mass of loaded cells thus prepared is then poured into an isotonic physiological solution for preservation and storage. When erythrocytes are used, it is practical to prepare the loaded cells in a potassium chloride solution and then to transfer the loaded cells into an isotonic sodium chloride solution that corresponds to blood serum in its ion concentration and osmolarity.

EXAMPLE I

Ferrite particles are prepared by the method described by W. J. Schnehle and V. D. Deetschreak in J. Appl. Phys. 32, 2355 (1961) by dissolving 1 mole of cobalt chloride and 2 moles of ferric chloride in 2 liters of hot distilled water and adding this with stirring to 1 liter of boiling 8-molar sodium hydroxide solution. The cobalt ferrite formed is then washed with water until neutralization is obtained, after which the large particles are filtered off. In order to prevent hemolysis or a disintegration of the loaded cells, after the incorporation of the ferrite particles into the loaded cells the ferrite particles are immediately after their formation coated with a silicone film by shaking the suspension containing the ferrite particles with silicone oil of the commercial designation AR5. After the separation of the excess silicone oil by centrifuging, the ferrite particles are suspended in a weight ratio of 1:10 in a solution of the following composition:

105 mM KCl; 20 mM NaCl; 4 mM $MgCl_2$; 7.6 mM $Na_2HPO_4$; 2.4 mM $NaH_2PO_4$ and 10 mM glucose.

In order to form the loaded cells erythrocytes are suspended in a solution of the composition just mentioned, quite independently from the solution used for the ferrite particles, in a ratio of about 1 part by volume of erythrocyte to 10 parts by volume of the solution. The pH value of the solution was 7.2.

10 ml of the suspension so formed containing the erythrocytes are exposed in a suitable apparatus for 40 microseconds at usec at 0° C. to an electric field strength of 12 KV/cm. About 1 minute after the application of the electric field, which caused hemolysis to take place, methotrexate was added in the ratio of 5 mM per liter of solution as well as 1 ml of the suspension containing the ferrite particles. After the hemolysis, which lasted about 5 minutes, the solution was held at 0° C. for another 5 minutes, in order to obtain an equilibrium between the medium located in the cell interiors and the external solution that contained the methotrexate. As the next step, the temperature of the solution was raised to 37° C., in order to accelerate the healing of the changes produced in the membranes by the electric field. The healing process was finished after about 20 minutes. In order to obtain the cells loaded with ferrite particles out of the suspension, the suspension was centrifuged several times for 2 minutes with an acceleration corresponding to 1,000 times the acceleration of gravity, the cell layer lying on the unenclosed particles being taken away each time.

The loaded cells thus obtained were next suspended in a physiological solution at a volume ratio of 1:10, of the composition:

13.86 mM NaCl; 12.3 mM $Na_2HPO_4$; 2.7 mM $NaH_2PO_4$.

The pH value of the solution was 7.4. A glass reagent container of a diameter of 10 mm was filled with the suspension thus obtained and the glass was brought between the pole pieces of a U shaped permanent magnet. As could be verified by means of a microscope, the loaded cells gathered on the reagent glass walls lying against the pole pieces.

After storage of the loaded cells at about 4° C. tests showed that after about 1 day, 90% of the loaded cells were still intact in the cell sediment, after 2 days 87%, after 4 days 65% and after 7 days still 53%.

EXAMPLE II

The loaded cells were produced as described in Example I, but instead of the solution containing the ferrite particles, 1 ml of a 10% isotonic ferritin solution was added to the solution containing the erythrocytes. After preparation of the loaded cells thus formed, the presence of ferritin locked in the cells was verified by means of an electron microscope.

EXAMPLE III

The loaded cells were formed as described in Example I, but, in addition to the methotrexate and the ferrite particles, there was also added 0.1 % by volume of albumin to the solution in which the erythrocytes were subjected to an electric field for increase of membrane permeability and hence for incorporation of the materials in the cells.

The loaded cells could be stored at a temperature of about 4° C. for a period of time longer than the loaded cells formed according to Example I could be stored. After 7 days, 85% of the loaded cells could still be detected in the cell sediment.

EXAMPLE IV

The loaded cells were prepared as in Example I, but instead of adding the solution containing the methotrexate and the ferrite particles to the solution containing the erythrocytes after the application of the electric field, a measured dose of sucrose and pronase P was added already before application of the electric field to the solution in which the erythrocytes had been placed. The dosing was such that the solution contained 10 mM of sucrose and 0.01 mg of pronase P per 100 ml of solution. The sucrose was marked with the radionuclide C 14. In order to follow the effect of the pronase P locked in the loaded cells, the loaded cells were preserved in a physiological solution of the composition given in the case of Example I, and then, after 20 hours, centrifuged off and the amount of the intact loaded cells determined by measuring the radio activity in the solution and in the still intact loaded cells. In comparison to the loaded cells that were prepared without the inclusion of pronase P, the proportion of cells that were still intact after 20 hours was only 11%.

EXAMPLE V.

The cells were prepared as in Example I, but instead of adding the solution containing the methotrexate and the ferrite particles after the application of the electric field, the methotrexate that was marked with tritium, albumin and phospholiphase C were added already before the application of the electric field. The methotrexate content of the solution was 5 mM, that of albumin 0.1% by volume and that of phospholiphase C 0.01 mg per 100 ml of solution.

After the formation of the loaded cells the effect of the phospholiphase C locked in the cells was determined by measurement of the radio activity—as in Example IV. After 20 hours, only 17% of the loaded cells remained intact, compared to the loaded cells that were prepared without inclusion of phospholiphase C.

EXAMPLE VI

For preparation of the loaded cells by the effect of osmotic pressure erythrocytes were suspended in a volume ratio of 1:1 in isotonic phosphate-buffered NaCl solution of the following composition:

138.6 mM NaCl; 12.3 mM $Na_2HPO_4$; 2.7 mM $NaH_2PO_4$.

The pH value of the solution was 7.4.

1 ml of the suspension thus formed was added with stirring to 10 ml of a solution that contained 5 mM of methotrexate that had been marked with tritium, 4 mM $MgSO_4$ and 50 mM of sucrose. Immediately thereafter 1 ml was added of a solution that contained 4 mM of $MgSO_4$, 50 mM of sucrose and ferrite particles in a weight ratio of 1:10. The solution so formed was allowed to stand for 5 minutes at 0° C.

As the next step, the osmolarity of the original solution was restored by adding a corresponding amount of 2-molar KCl solution. The solution was then allowed to stand at 0° C. for another 5 minutes and then the temperature was raised for 20 minutes to 37° C., in order to accelerate the healing up of the membranes. After centrifuging out of the solution the loaded cells thus produced, the cells were incubated in an isotonic phosphate-buffered NaCl solution of the previously mentioned composition.

The loaded cells thus produced contained practically the same quantity of methotrexate per unit volume as did the external medium, namely 98% of the concentration of methotrexate present in the external medium.

The determination of the effect of the ferrite particles incorporated in the cells was done as described in Example I.

Although the invention has been described with reference to several illustrative examples, it will be understood that variations are possible within the inventive concept.

Just as loaded cells prepared according to previously known methods have been used for releasing medicaments and the like in the blood stream of animals and of human beings, the present invention is likewise applicable for release of such materials in the blood stream of human beings as well as of other animals with the particular advantages available only by the practice of the present invention.

The terms "animal cells" and "animal body" as used herein, except in reference to specific experiments already performed, therefore, are to be understood as generally including human cells and a human body, respectively.

We claim:

1. A process for preparing a mass of loaded cells suspended in a solution which cells by their loading are provided with material intended for chemical or physical interaction with substances present outside the cells, comprising the steps of suspending living animal cells, selected from the group consisting of blood cells and liver cells, and having cell membranes, in a cell-compatible solution, increasing the permeability of the cell membrances by the effect of osmotic pressure, or by the effect of an electric field, or both, incorporating an agent selected from the group of tumor-treating agents, medicaments and radionuclides into the cells by passage of said agent from a cell-compatible solution through the membranes of increased permeability, restoring the original permeability of the membranes by healing up the membranes by regeneration effect, then separating the cells from the solution in which they were suspended and putting them for preservation in suspension in a physiological solution of the same osmolarity as the loaded cell content, said process incorporating the improvement consisting in that:

in the step of incorporating said selected agent into the cells from a cell-compatible solution, there is provided in the cell-compatible solution and therefrom incorporated into the cells at least one magnetic compound, containing combined oxygen as well as at least one metal, in the form of particles of a diameter lying in the range from 1 to 20 nm previously coated with a silicone film in sufficient dosing to enable the loaded cells as prepared in accordance with the process and suspended in a physiological solution, to be gathered and held at a predetermined location in the physiological solution by the application of a magnetic field by means external to the physiological solution.

2. A process as defined in claim 1, in which said selected agent is an antitumor agent which includes a first material which if incorporated alone in the loaded cells would lead to premature destruction of the cell membranes by interaction therewith, and in which in the step of incorporating said antitumor agent and said magnetic particles into the cells, there is also incorporated in the cells a substance selected from the group of proteins and sugars for inhibiting the cell-destructive effect of said first material by the forming of hydrogen-bridge-bonds or covalent bonds therewith so as to inhibit the reaction of said first material with the cell membranes without impairing the intended activity of said antitumor agent, said inhibiting substance being provided in such dosing in the cell-compatible solution utilized in said step of incorporating said agent, substance, and magnetic particles into the cells, that after the conclusion of said incorporating step and the performance of the step of restoring the original permeability of the membranes, the interaction of said antitumor agent with the cell membranes is prevented for a predetermined period of time.

3. A method as defined in claim 1, in which said selected agent is an antitumor agent having no destructive effect upon the cell membranes and in which in the step of incorporating said selected agent and said magnetic particles into the cells, in a cell-compatible solution, there is provided in said solution and incorporated into the cells an enzyme having a destructive effect on the cell membranes that is provided in such dosing that, after the performance of said incorporating step and also of the step of restoring the original permeability of the membranes, the cell membranes of the loaded cells will be destroyed after a predetermined time.

4. A process as defined in claim 2, in which in the step of incorporating said selected agent, said magnetic particles and said inhibiting substance into the cells in a cell-compatible solution, there is provided in the cell-compatible solution and incorporated into the cells also an enzyme having a destructive effect on the cell membrane which is provided in such dosing in said cell-compatible solution that, after the step of incorporating said agent, magnetic particles, substance and enzyme into the cells and after performance of the step of restoring the original permeability of the membranes, the cell membranes of the loaded cells will be destroyed after a predetermined period of time.

5. A suspension of loaded cells in a physiological solution in which said loaded cells are animal cells selected from the group consisting of blood cells and liver cells and are loaded with at least two materials extraneous to the original cell content, said material including a first material which is an agent selected from the group consisting of tumor-treating agents, medicaments and radionuclides and a second material which is a ferrimagnetic, ferromagnetic or paramagnetic compound, containing combined oxygen as well as at least one metal, in the form of particles having a diameter in the range between 1 and 20 nm coated with a silicone film and present in said loaded cells in sufficient quantity to enable said loaded cells to be gathered and held at a predetermined position in a physiological solution by the application of a magnetic field by means external to said physiological solution.

6. A suspension of loaded cells in a physiological solution as defined in claim 5, in which said first material is an antitumor agent having a destructive effect on the cell membranes and in which said loaded cells contain also a third material selected from the group consisting of sugars and proteins for forming hydrogen bonds or covalent bonds with said first material and thereby inhibiting the destruction of said cell membranes, said third material being in such dosing that the destruction of the cell membranes is thus inhibited for a predetermined period of time.

7. A suspension of loaded cells in a physiological solution as defined in claim 6 in which said loaded cells contain also a fourth material selected from the group consisting of proteolytic enzymes and enzymes destructive of lipids, for exerting a destructive effect on the membranes of the loaded cells, said fourth material being provided in such dosing that combined effect of said third and fourth materials is such that the membranes of the loaded cells will be destroyed after a predetermined period of time following completion of the preparation of said suspension of loaded cells.

8. A suspension of loaded cells in a physiological solution as defined in claim 5 in which said selected agent is a cell-compatible material having no destructive effect on the membranes of said loaded cells and in which there is also incorporated in said loaded cells a third material selected from the group of proteolytic enzymes and enzymes destructive of lipids, for exerting a destructive effect on the membranes of the loaded cells, that is present in such dosing that membranes of the loaded cells will be destroyed after a predetermined period of time following the preparation of the suspension of loaded cells.

9. A suspension of loaded cells in a physiological solution as defined in claim 8 in which there is incorporated in the loaded cells also a fourth material selected from the group consisting of proteins and sugars for forming hydrogen bonds or covalent bonds with said third material, said fourth material being provided in such dosing that the combined effect of said third and fourth materials will produce the destruction of the membranes of the loaded cells after a predetermined period of time following the preparation of the suspension of loaded cells.

10. A suspension of loaded cells as defined in claim 5, in which said second material consists of particles of a substance selected from the group consisting of ferritin, magnetite and ferrites, provided with a coating of a silicone film.

11. A suspension of loaded cells as defined in claim 6, in which said second material consists of a particles of a substance selected from the group consisting of ferritin, magnetite and ferrites, provided with a coating of a silicone film.

12. A suspension of loaded cells as defined in claim 7, in which said second material consists of particles of a substance selected from the group consisting of ferritin, magnetite and ferrites, provided with a coating of a silicone film.

13. A suspension of loaded cells as defined in claim 8, in which said second material consists of particles of a substance selected from the group consisting of ferritin, magnetite and ferrites, provided with a coating of a silicone film.

14. A suspension of loaded cells as defined in claim 9, in which said second material consists of particles of a substance selected from the group consisting of ferritin, magnetite and ferrites, provided with a coating of a silicone film.

* * * * *